(12) United States Patent
Van Gompel et al.

(10) Patent No.: US 6,193,701 B1
(45) Date of Patent: Feb. 27, 2001

(54) PERSONAL CARE ARTICLE HAVING ZONES WITH DIFFERENT RESISTANCE-TO STRETCH

(75) Inventors: Paul Theodore Van Gompel, Hortonville; Yung Hsiang Huang, Appleton; Georgia Lynn Zehner, Larsen, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/001,895

(22) Filed: Dec. 31, 1997

(51) Int. Cl.$^7$ .............................. A61F 13/15; A61F 13/20
(52) U.S. Cl. ................... 604/385.01; 604/370; 604/378; 604/385.27
(58) Field of Search .............................. 604/385.1, 385.2, 604/394, 358, 385.01, 385.16, 385.24, 385.22

(56) References Cited

U.S. PATENT DOCUMENTS

| | | | |
|---|---|---|---|
| 4,486,192 | 12/1984 | Sigl | 604/385 |
| 4,701,171 | 10/1987 | Boland et al. | 604/385 A |
| 4,720,415 | 1/1988 | Vander Wielen et al. . | |
| 4,726,807 | 2/1988 | Young et al. | 604/385 A |
| 4,747,846 | 5/1988 | Boland et al. | 604/38 A |
| 4,756,709 | * 7/1988 | Stevens | 604/385 |
| 4,854,985 | 8/1989 | Soderlund | 156/85 |
| 4,857,067 | 8/1989 | Wood et al. | 604/389 |
| 4,872,871 | * 10/1989 | Proxmire et al. | 604/394 |
| 5,151,092 | 9/1992 | Buell et al. . | |
| 5,376,198 | 12/1994 | Fahrenkrug et al. . | |
| 5,486,273 | 1/1996 | Widlund et al. | 264/154 |
| 5,569,232 | 10/1996 | Roe et al. | 604/385.2 |
| 5,658,269 | 8/1997 | Osborn, III et al. . | |
| 5,662,634 | 9/1997 | Yamamoto et al. . | |
| 5,846,232 | * 12/1998 | Serbiak et al. | 604/385.2 |

FOREIGN PATENT DOCUMENTS

| | | |
|---|---|---|
| 1471174 | 12/1965 | (FR) . |
| 2 297 473 | 6/1996 | (GB) . |
| WO 95/14453 | 6/1995 | (WO) . |
| WO 97/43994 | 11/1997 | (WO) . |

* cited by examiner

Primary Examiner—John G. Weiss
Assistant Examiner—Michele Kidwell
(74) Attorney, Agent, or Firm—Thomas D. Wilhelm; Michael L. Winkelman

(57) ABSTRACT

A personal care article includes a resiliently stretchable outer cover. In a first embodiment, a first zone of the outer cover is embossed forming a pattern of embossments providing a first set of desired properties pertaining to stretch of a portion of the outer cover. A second zone of the outer cover is not modified to provide the first set of properties and thus has different stretch properties than the first zone. In a second embodiment, a first panel is secured to a resiliently extensible second panel. A first zone of the second panel can have a pattern of embossments securing the second panel to the first panel. The embossments cause the first zone to have different stretch properties than a second zone of the second panel that is not embossed thereby to impart the set of stretch properties. In a third embodiment the second panel is pre-stretched to a predetermined degree of elongation before securement to the first panel. In use, the personal care article then has a first characteristic load/extension relationship until the article reaches the predetermined degree of elongation and a second load/extension relationship as the article is extended beyond the predetermined degree of elongation of the second panel.

74 Claims, 10 Drawing Sheets

PERSONAL CARE ARTICLE HAVING ZONES WITH DIFFERENT RESISTANCE-TO STRETCH

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Personal care articles such as infant diapers, training pants, adult incontinence products, and the like are well known. Such articles have achieved a wide acceptance due to their ability to receive and absorb body exudates. This invention pertains to personal care articles and especially to their stretch characteristics at different zones of the respective personal care articles. For instance, a personal care article should have a desired stretchability, resistance to stretch, and resilience, across waistband sections or adjacent leg openings.

BACKGROUND OF THE INVENTION

In general, personal care articles should comfortably fit the body of a wearer. Conventional personal care articles are made using materials for e.g. an outer cover and a bodyside liner, thus to make a substrate which is generally non-stretchable, or stretchable only to a limited degree such as up to no more than about 50%. Thus, the primary substrate materials, from which such personal care articles are made, lack resilient stretch characteristics which are desired at the waist and at the leg openings. Accordingly, conventional personal care articles generally have resiliently stretchable waist elastic elements secured about the waistbands of the articles. Likewise, personal care particles generally have leg elastic elements disposed at opposing sides of the crotch portion adjacent leg cutouts. Such waist elastics elements and leg elastics elements are used to provide desired levels of extensibility and retractability to the personal care articles in the waistband region, and in the crotch portion, respectively.

When, as in the personal care articles of the invention, one or more of the materials used to make the outer cover and the bodyside liner is resiliently stretchable greater than 50%, e.g. up to at least 300%, it is still desirable to provide the same amounts for stretch, resistance to stretch, and resilience, as are provided for in conventional personal care articles. Thus, while resilient stretchability is desired in the waist and leg areas, too much stretch, or too little resistance to stretch, are no more acceptable than too little stretch or too much resistance to stretch. Accordingly, where the amount of stretch is greater than desired, or where the resistance to stretch is less than desired, in e.g. a stretchable outer cover or a stretchable bodyside liner, suitable modifications to the respective outer cover or bodyside liner should be made in order to provide the desired level of stretchability, and resistance to stretch.

SUMMARY OF THE DISCLOSURE

Applicants' invention defined herein, provides the desired level of resilient stretch, and the desired resistance to stretch in personal care articles which include resiliently stretchable outer covers and/or resiliently stretchable bodyside liners. Such stretchable elements are embossed to provide the desired levels of stretch in the selected areas. For example, stretch in the waistband section can be reduced by embossing the stretch outer cover in the waist area. Such embossing increases the resistance-to-stretch in the embossed area whereby the resistance to stretch in the embossed area is greater than the resistance-to-stretch in other zones of the article.

Therefore, unlike the addition of elastomeric elements, or treatment of materials to increase stretch, as was known in the prior art, in applicants' products and processes, modifications are made to the materials used in the personal care articles of the invention thereby to decrease the amount of stretch or elasticity, thus to increase the resistance to stretching, in the so-treated areas or zones of the personal care articles of the invention.

Thus, the present invention relates to a personal care article comprising an outer cover resiliently stretchable in at least one direction. At least a first portion of a first zone of the resiliently stretchable outer cover has a pattern of embossments, effective to reduce or otherwise limit or control stretching of the outer cover in the first zone, thereby to provide a first set of desired properties pertaining to the amount of stretchability, and resistance to stretch of the outer cover. The outer cover has a second separate and distinct zone wherein the outer cover is not modified to provide the first set of limitations. The embossments in the first zone thus cause the so-treated portion of the outer cover in the first zone to have a different resistance-to-stretch than the respectively untreated, or lesser treated, portion of the outer cover in the second zone.

In some embodiments, the outer cover has resilient stretchability in at least the cross-direction in the front portion of the personal care article, the outer cover having a first waistband section in the front portion and a second waistband section in the rear portion, the first zone comprising the first waistband section in the front portion of the personal care article, the first waistband section providing the first set of desired stretch properties pertaining to the amount of stretch in the waistband section.

In some embodiments, the second zone comprises an area of the outer cover spaced inwardly from the first waistband section.

In some embodiments, the personal care article is devoid of added waist elastic elements.

In some embodiments, the outer cover is resiliently stretchable in at least the cross-direction in the rear portion of the personal care article, a second waistband section comprising a third zone in the rear portion having a greater resistance-to-stretch than the second zone.

In some embodiments, the outer cover includes a fourth zone and a fifth zone, effectively embossed at portions thereof such that the fourth and fifth zones have greater resistance-to-stretch than the second zone.

In some embodiments, the fourth zone is adjacent a first outer edge at least in the crotch portion and the fifth zone is adjacent a second opposing outer edge at least in the crotch portion, the fourth and fifth zones optionally extending along the length of the crotch portion in the longitudinal direction.

In some embodiments, the personal care article is devoid of added leg elastic elements in the crotch portion, the fourth and fifth zones providing the properties of leg elastic elements.

In some embodiments, the first zone comprises a plurality of spaced embossments forming an array of such embossments.

In some embodiments, the array comprises at least two rows of spaced points. In other embodiments, the array comprises a series of spaced lines or other configurations.

In some embodiments, the personal care article has a front edge at the front portion, and a rear edge at the rear portion, the outer cover being substantially unfolded at the front edge and the rear edge.

In some embodiments, the personal care article includes an absorbent structure superposed on and operably connected to the outer cover, thereby to form an absorbent personal care article, the absorbent structure including a substantially liquid impermeable backsheet, a liquid permeable bodyside liner superposed on the backsheet, and an absorbent core disposed between the bodyside liner and the backsheet.

In some embodiments, extendible attachment elements secure the absorbent structure to the outer cover while allowing resilient stretching of the outer cover along the cross-direction.

In some embodiments, the extendible attachment elements each have at least one pleat that connects the absorbent structure to the outer cover.

In some embodiments, the outer cover is intermittently embossed in the first zone.

In another embodiment, the personal care article comprises a first panel, a second panel resiliently stretchable in at least one direction, the second panel being in surface-to-surface relationship with the first panel, the first and second panels, in combination, defining a substrate, a first portion of a first zone of the second panel having a pattern of embossments securing the second panel to the first panel and thereby providing a first set of desired properties pertaining to stretch of the second panel, a second zone of the second panel wherein the second panel does not exhibit embossments securing the second panel to the first panel or the first set of properties, the embossments in the first zone thus causing the first zone to have a different resistance-to-stretch than the second zone.

In some embodiments, the second panel is unstretched when secured to the first panel.

In some embodiments, the first zone comprises at least part of the crotch portion of the personal care article, the first zone at the crotch portion having a greater resistance-to-stretch than the second zone.

In some embodiments, the first panel comprises an extensible bodyside liner and the second panel comprises an outer cover.

In some embodiments, the first panel comprises a substantially non-extensible bodyside liner.

In some embodiments, the outer cover is pre-stretched in at least one direction when secured to the bodyside liner.

In some embodiments, the outer cover is pre-stretched to a predetermined degree of elongation before securement to the bodyside liner, the substrate having a first characteristic load/extension curve relationship when stretched to the predetermined degree of elongation, and a second different characteristic load/extension relationship when stretched beyond the predetermined degree of elongation.

In some embodiments, the pattern of embossments in the first zone controls the resistance-to-stretch of the personal care article in the first zone. For example, in some embodiments, the first zone comprises between about 2% and about 50% of the overall area, preferably between about 5% and about 40% of the overall area, and most preferably between about 10% and about 30% of the overall area, of the second panel.

In some embodiments, approximately about 5% to about 80% of the surface area in the first zone of the second panel is embossed to the first panel.

In some embodiments, the embossments provide bonding of the second panel to the first panel as a pattern of spaced points extending in two dimensions across substantially the entirety of the first zone.

In some embodiments, the bonding comprises ultrasonic bonding of the second panel to the first panel.

In other embodiments, the embossments comprise adhesive bonding of the second panel to the first panel.

In some embodiments, the second panel is elongated no more than about 350% and not less than about 5%, preferably no more than about 200% and not less than about 10%, most preferably no more than about 100% and not less than about 15%, when secured to the first panel.

Other embodiments of the invention comprehend methods of imparting first and second different sets of stretch properties to respective first and second different zones of a substrate of a personal care article, the substrate including a first panel and a second resiliently stretchable panel, including securing the first panel in surface-to-surface relationship with the second panel by effectively embossing at least portions of a first zone of the second panel to respective portions of the first panel, the embossing causing the first zone of securement to have a first set of desired stretch properties different from a second set of stretch properties in a second zone of the substrate.

Figure 1:
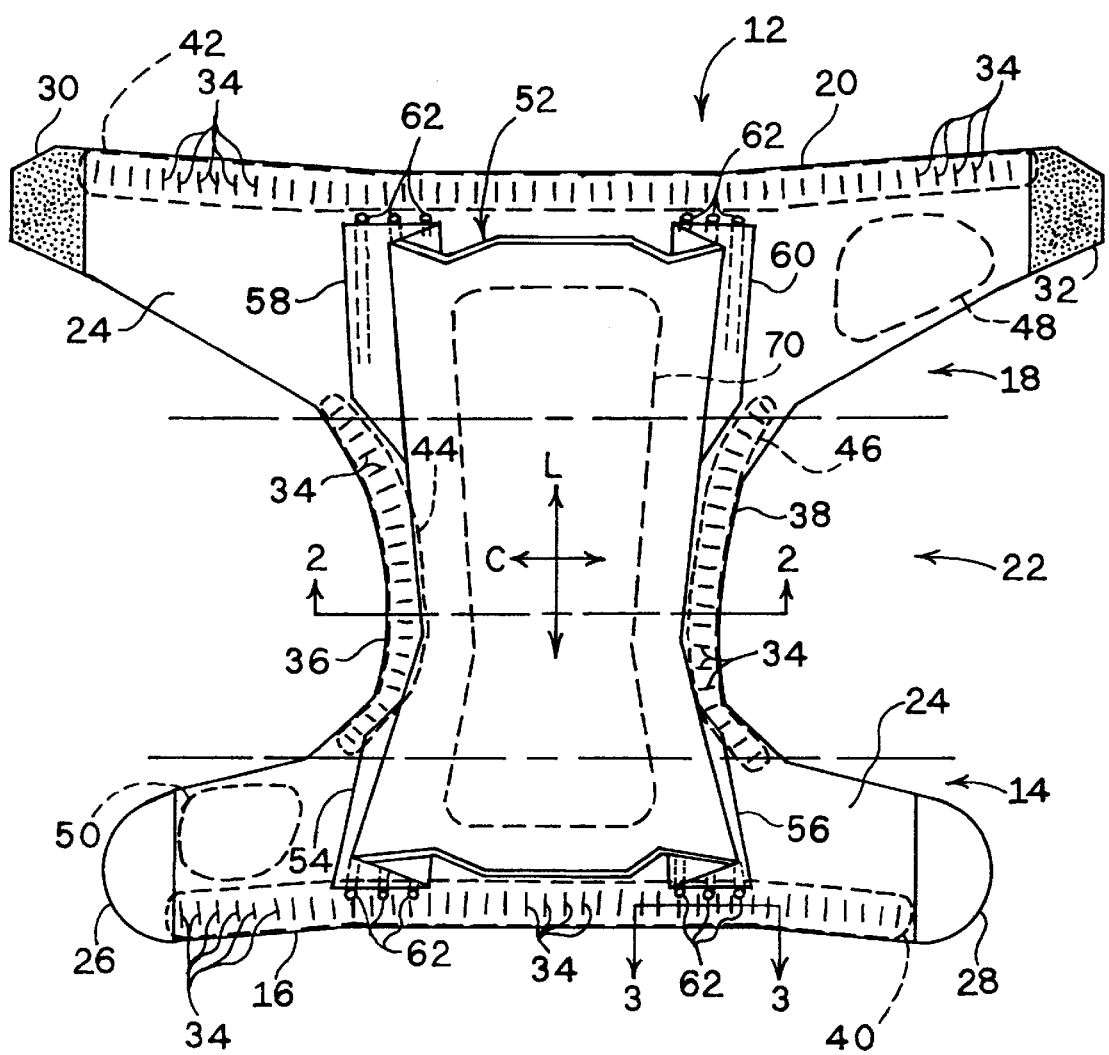
FIG. 1 shows a top view of a first embodiment of personal care articles of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in disposable personal care articles, but it should be understood that potential uses of the structures of the present invention need not be limited to the context of disposable personal care articles, such as diapers, feminine care articles, incontinence garments, and the like.

As used herein and in the claims that follow, the phrase "personal care article" includes adult incontinence articles, feminine hygiene products, articles which have no significant absorbent function but which receive and/or store urine and/or fecal material, articles which do have a significant absorbent function and which receive and/or store urine and/or fecal material, such as diapers, training pants, and the like.

As used herein and in the claims that follow, the phrase "resistance-to-stretch" is an expression of the load/extension ratio and means the amount of force required to elongate a panel or other material a certain distance. Thus, a first zone having a greater resistance-to-stretch than a second zone requires the application of a greater force to elongate the first zone the same distance as the second zone elongates under application of a lesser force.

As used herein and in the claims that follow, "embossing" or "embossment" includes areas where a material is acted upon by pressure, thermal energy, ultrasonic energy, or other treatment including thermoforming, and applying adhesives to bond first and second panels at selected areas, thereby to change the stretch properties of the material at the locus of such action. Other bonding techniques for securing first and second panels to each other are also within the scope of the term "embossing". Such techniques lock up stretch in the second panel due to securement to the first panel at various areas thereof.

Personal care article 12 having a longitudinal direction "L" and a cross-direction "C". shown in FIG. 1, includes a front portion 14 having a front edge 16, a rear portion 18 having a rear edge 20, and a crotch portion 22 between front portion 14 and rear portion 18. Longitudinal direction "L" represents a direction along the length of personal care article 12. Cross-direction "C" represents a direction across the width of personal care article 12. Personal care article 12 includes an outer cover 24. Grasping panels 26, 28 are secured to outer cover 24 at opposing end regions of front portion 14 as shown in FIG. 1. Fastener apparatus 30, 32 at opposing end regions of rear portion 18 fasten the opposing end regions of rear portion 18 to front portion 14.

As shown in FIG. 1, embossments 34 in outer cover 24 are disposed in front portion 14 adjacent front edge 16 and in rear portion 18 adjacent rear edge 20 of the outer cover. Embossments 34 are also disposed adjacent opposing edges 36, 38 in crotch portion 22 of personal care article 12. Embossments 34 provide a first set of zones 40, 42, 44, 46 having a different resistance-to-stretch than a second set of zones 48, 50 of outer cover 24 which contain no embossments. While zones 48, 50 represent specific areas of outer cover 24 containing no embossments, essentially the entire outer cover comprises a single combined zone having no embossments except for zones 40, 42, 44, 46.

However, in some embodiments, at least portions of unembossed zones 48, 50 can contain nominal embossments. Such embossments provide less resistance-to-stretch than the embossments in first set of zones 40, 42, 44, 46.

Absorbent structure 52 is superposed on and operably secured to outer cover 24 to form an absorbent article. Absorbent structure 52 includes extendible attachment elements 54, 56, 58, 60 secured by adhesive 62 to respective portions of outer cover 24.

Figure 2:
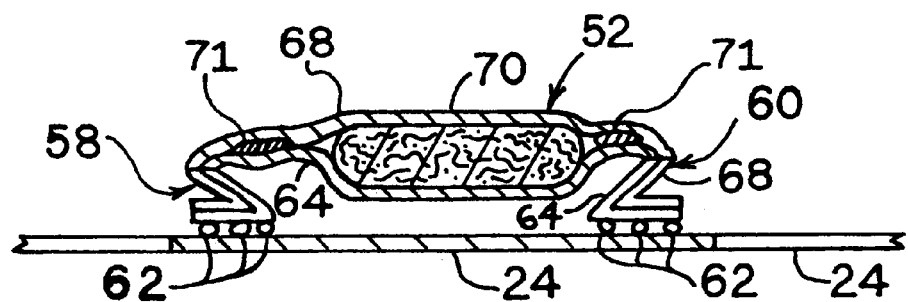
FIG. 2 shows a cross-sectional view of the personal care article of FIG. 1 taken at 2—2 of FIG. 1.

As better shown in FIG. 2, absorbent structure 52 includes a substantially liquid impermeable backsheet 64, a liquid permeable bodyside liner 68 superposed on backsheet 64, and an absorbent core 70 disposed between the backsheet and the bodyside liner. As better shown in FIG. 1, absorbent structure 52 is secured to outer cover 24 in front portion 14 by extendible attachment elements 54, 56, and in rear portion 18 by extendible attachment elements 58, 60. As shown in FIG. 2, rear extendible attachment elements 58, 60 are extensions of the combination of backsheet 64 and bodyside liner 68, and have pleated folds between absorbent core 70 and outer cover 24. The pleated folds permit extension of personal care article 12 in the cross-direction "C" without stressing absorbent core 70 or bodyside liner, 68.

Outer cover 24 preferably comprises a material resiliently stretchable in at least the cross-direction over at least about 30% of the entire surface area of the outer cover from an at-rest condition. Generally, outer cover 24 is resiliently stretchable in at least front portion 14 of personal care article 12. In some embodiments, outer cover 24 can be resiliently stretchable in front portion 14 and rear portion 18 of personal care article 12. Outer cover 24 can also be resiliently stretchable in at least one direction over the entirety of the outer cover.

In other embodiments, outer cover 24 can be resiliently stretchable in both cross-direction "C" and longitudinal direction "L". Thus, in certain embodiments, the entirety of the outer cover can be extended along longitudinal direction "L" and cross-direction "C" to fit personal care article 12 to a wearer.

Outer cover 24 can include an elastomeric material which provides to the outer cover from about 10% to about 300% elongation within a tension range comfortable to the wearer. In preferred embodiments, outer cover 24 can have an elongation of at least about 30 percent when subjected to a tensile force load of 80 grams per lineal centimeter width of the outer cover transverse to the stretch direction. Outer cover 24 can include a material comprising a film, laminate (film-to-nonwoven), a nonwoven elastomer, or a combination thereof.

The phrase "resiliently stretchable" means the ability of a material to elongate or stretch in response to a force and, after release of the force, to return to substantially its unstretched dimension without significant long term deformation of the material. For example, an exemplary outer cover 24 can be elongated 200% by a force (three times its original length) and then return to about 150% of its original length after release of the force. Such a recovery of at least about 75% of the amount of the extension describes a resiliently stretchable outer cover.

Elastomers useful in outer cover 24 include thermoplastic elastomers, copolymers and block copolymers (butadienes and the like), polyesters, and ethylene vinyl acetates, and cross-linked and cured elastomers such as rubbers.

The elastomers can be fabricated into continuous or apertured films varying from about 0.2 mils up to about 5 mils in thickness. The elastomers can also be nonwovens or meltblown polymers having basis weights varying from about 5 grams per square meter to about 250 grams per square meter. Composites of elastomers and nonwovens or films can be combined by e.g. adhesive bonding, thermal bonding, or ultrasonic bonding of multiple layers to form multiple layer laminates. The outer cover materials can comprise nonwoven materials thermally or otherwise bonded to elastomeric films or layers or laminates of meltblown materials, such as stretch-bonded laminates or neck-bonded laminates.

An exemplary neck-bonded laminate for outer cover 24 includes a 45 gram per square meter G2755 KRATON® elastomeric film, commercially available from Shell Chemical Company. The film is disposed between, and bonded to, two 23 gram per square meter layers of 40% necked polypropylene spunbonded nonwoven fabrics. Examples of neck-bonded laminates are described in U.S. Pat. No. 5,226,992 issued Jul. 13, 1993 to Morman, the disclosure of which is hereby incorporated by reference in its entirety in a manner that is consistent (not contradictory) herewith.

Outer cover 24 can comprise, for example, suitable meltblown elastomeric fibrous webs as described in U.S. Pat. No. 4,663,220 issued May 5, 1987 to T. Wisneski et al, and hereby incorporated by reference in its entirety in a manner that is consistent (not contradictory) herewith. Examples of composite fabrics comprising at least one layer of a nonwoven material secured to a fibrous elastic layer are described in European Patent Application No. EP 0110010 published on Apr. 8. 1987 with the inventors listed as J. Taylor et al., the disclosure of which is hereby incorporated by reference in its entirety in a manner that is consistent (not contradictory) herewith.

In a particular embodiment wherein outer cover 24 includes an elastomeric material, it is desirable that the outer cover be capable of accommodating an elongation in the cross-direction of at least about 5 percent, more desirably at least about 15 percent, and even more desirably at least about 30 percent when subjected to a tensile force load of 80 grams in the cross-direction per lineal centimeter of the sample measured in the longitudinal direction. Moreover, it is also desirable that outer cover 24 be capable of providing a tension range of from about 20 to about 400 grams, more desirably from about 40 to about 275 grams, and even more desirably from about 60 to about 200 grams per lineal centimeter of the sample measured in the longitudinal direction when subjected to an elongation of 30 percent in the cross-direction.

In another embodiment of the invention, outer cover 24 can be a nonwoven, spunbonded polypropylene fabric composed of, or formed into, a web. The fabric can be creped or necked such that it is extensible in at least one of longitudinal direction "L" and cross-direction "C". Other materials having other advantageous characteristics are also useful as outer cover 24.

In other embodiments, outer cover 24 can comprise a stretch-bonded laminate material having appropriate resilient stretchability. A stretch-bonded laminate comprises at least a two-layered composite in which one layer is a gatherable layer and the other layer a stretchable layer. The layers are joined together when the stretchable layer is in a stretched condition so that, upon relaxing the composite of the joined layers, the gatherable layer is gathered. Other suitable materials also can be utilized for outer cover 24.

Grasping panels 26, 28 are preferably nonstretchable, and may be formed from a material separate from outer cover 24, and then assembled and attached to outer cover 24 at opposing ends of front portion 14 of personal care article 12. Grasping panels 26, 28 extend outwardly from outer cover 24 to form a pair of opposed waist flap sections. Grasping panels 26, 28 assist a user in applying personal care article 12 to the body of the wearer.

Grasping panels 26, 28 can be secured to outer cover 24 by e.g. ultrasonic bonding. Grasping panels 26, 28 can also be secured to outer cover 24 by adhesives, stitching, thermal bonding, clips, staples, solvent bonding or the like Grasping panels 26, 28 comprise substantially non-stretchable material,.such as substantially non-stretchable polymer films, woven fabrics, non-woven fabrics, or the like, as well as combinations thereof. Fastener apparatus 30, 32 may be formed from separate materials that are then assembled and attached to outer cover 24 at opposing ends of rear portion 18 of personal care article 12. Fastener apparatus 30, 32 typically comprise substantially nonelastomeric fastener material. Fastening apparatus 30, 32 extend outwardly from outer cover 24 to form a pair of opposed fastening sections. In use, fastening apparatus 30, 32 secure rear portion 18 to front portion 14 and thus retain personal care article 12 on the body of the wearer.

Fastener apparatus 30, 32 can be permanently secured to outer cover 24 by ultrasonic bonding. Fastener apparatus 30, 32 also can be secured to outer cover 24 by adhesives, stitching, thermal bonding, clips, staples, solvent bonding or the like.

Fastener apparatus 30, 32 can include, for example, hooks of a hook and loop fastening system. Other well known fastening systems can be used to support personal care article 12 on the wearer. For example, a cohesive fastening system, an adhesive fastening system, or the like may be utilized, in combination with suitable cooperating elements on front portion 14, as necessary, to support personal care article 12 on the wearer.

In use, fastener apparatus 30, 32 are preferably secured to a resiliently stretchable landing zone in front portion 14 of outer cover 24 thereby securing the respective fastener apparatus 30, 32 to the resiliently stretchable landing zone. An example of a fastener apparatus suitable for use in the subject invention is set forth in U.S. Pat. No. 5,399,219 issued Mar. 21, 1995 to Roessler et al, the disclosure of which is hereby incorporated by reference in its entirety in a manner that is consistent (not contradictory) herewith.

Preferably, outer cover 24 comprises a material having suitably looped construction such that hooks of fastener apparatus 30, 32 engage directly to the fabric of outer cover 24. Thus, in preferred embodiments, outer cover 24 acts as a landing zone for fastener apparatus 30, 32. Such an arrangement helps control the number of elements that must be formed, placed, and secured on personal care article 12.

Absorbent structure 52 includes liquid impermeable backsheet 64, permeable bodyside liner 68, absorbent core 70, and extendible attachment elements 54, 56, 58, 60.

Extendible attachment elements 54, 56, 58, 60 comprise outwardly extending sections of backsheet 64 and bodyside liner 68, extending outwardly at opposing sides of the front and rear of absorbent structure 52 as shown in FIGS. 1–2. Extendible attachment elements 54, 56, 58, 60 each have a folded or pleated section. The extendible attachment elements are secured by adhesive 62 to outer cover 24. Thus extendible attachment elements 54, 56, 58, 60 secure absorbent structure 52 to outer cover 24 while accommodating resilient stretching of front portion 14 and rear portion 18 of outer cover 24 along at least cross direction "C". Each of extendible attachment elements 54, 56, 58, 60 have at least one pleat folded therein, connecting absorbent structure 52 and outer cover 24. The pleat or pleats open and extend when personal care article 12 is extended in cross-direction "C". Thus extendible attachment elements 54, 56, 58, 60 generally isolate absorbent structure 52 from modest amounts of movement and/or extension of outer cover 24, thereby to accommodate extensibility of at least front portion 14, of the outer cover, in cross-direction "C".

In the embodiment of FIG. 1, the combination of backsheet 64 and bodyside liner 68 can have limited extensibility or no extensibility because the pleats of extendible attachment elements 54, 56, 58, 60 can open and unfold sufficiently to accommodate stretching of outer cover 24 in cross-direction "C" such as for securement to a wearer.

Extendible attachment elements 54, 56, 58, 60 can comprise separate elements (not shown) secured to at least one of backsheet 64 and bodyside liner 68. Materials suitable for use in separate extendible attachment elements 54, 56, 58, 60 include polyester, foams, and natural fibers. Various other woven and nonwoven fabrics can be used in extendible attachment elements 54, 56, 58, 60. Instead of having pleats, extendible attachment elements 54, 56, 58, 60 can comprise extensible, preferably resiliently extensible elements that can stretch or extend significantly in at least cross-direction "C".

Liquid impermeable backsheet 64 can comprise a single layer, or multiple components, multiple layers, or partial layers, of material, such that the resulting backsheet is substantially impermeable to liquids. A typical backsheet 64 may be manufactured from a thin plastic film or other flexible liquid-impermeable material. For example, impermeable backsheet 64 can be formed from a polyethylene film, or a polyethylene film laminated to a surface of a nonwoven web, such as a spunbonded web of polyolefin fibers. Further, liquid impermeable backsheet 64 can be formed of a woven or nonwoven fibrous web which has been totally or partially constructed or treated to impart a desired level of liquid impermeability to selected regions that are adjacent or proximate absorbent core 70. Still further, liquid impermeable backsheet 64 may optionally be composed of a micro-porous material which permits vapors to escape from absorbent core 70 while preventing liquid exudates from passing through the backsheet.

Bodyside liner 68 comprises a skin-facing surface which is compliant, soft-feeling, and non-irritating to the wearer's skin. Further, bodyside liner 68 should be sufficiently porous to be liquid permeable, permitting liquid to penetrate through its thickness.

Bodyside liner 68 may be composed of a substantially hydrophobic and substantially nonwettable material, with the hydrophobic material preferably being treated with a surfactant or otherwise processed to impart a desired level of wettability and hydrophilicity.

Bodyside liner 68 may be manufactured from a wide selection of web materials, such as porous foams, reticulated foams, apertured plastic films or natural or synthetic fibers. For example, bodyside liner 68 may comprise wood or cotton fibers. Other useful materials are synthetic fibers, such as polyester or polypropylene fibers, or a combination of natural and synthetic fibers. Bodyside liner 68 is suitably utilized to help isolate, from the wearer's skin, the liquids held in absorbent core 70.

Various woven and nonwoven fabrics can be used for bodyside liner 68. For example, bodyside liner 68 may be composed of a meltblown or spunbonded web of polyolefin fibers. Bodyside liner 68 may also comprise a carded and/or bonded web composed of natural and/or synthetic fibers.

In a particular embodiment of the present invention, bodyside liner 68 may comprise a spunbonded polypropylene fabric composed of about 2.8–3.2 denier fibers formed into a web having a basis weight of about 22 grams per square meter and a density of about 0.06 grams per cubic centimeter. A preferred fabric is treated with about 0.3 weight percent of a surfactant.

Bodyside liner 68 can be formed from a single layer, or may comprise a multiplicity of components, layers, or partial layers, which correspond to any of the materials disclosed herein for the bodyside liner, as well as others known in the art.

Absorbent core 70, when used in personal care articles 12 of the invention, may be manufactured from a wide variety of materials in a wide variety of sizes, and in a wide variety of shapes such as rectangular, trapezoidal, T-shape, I-shape, hourglass shape, etc. The size, and absorbent capacity of absorbent core 70 should be compatible with the size of the intended wearer and the anticipated liquid loading to be imparted by the intended use of personal care article 12.

Absorbent core 70 suitably comprises a matrix of hydrophilic fibers, such as a web, or webs, of cellulosic fluff, preferably in combination with a high-absorbency material commonly known as superabsorbent material. In a preferred embodiment, absorbent core 70 comprises a mixture of superabsorbent hydrogel-forming material and wood pulp fluff. In place of the wood pulp fluff, one may use synthetic, polymeric, or meltblown or natural fibers or a combination of wood pulp fluff, synthetic fibers, polymeric fibers, meltblown fibers, and/or natural fibers. The superabsorbent material may be substantially homogeneously mixed with the hydrophilic and/or hydrophobic fibers, or other materials, or may be otherwise combined into absorbent core 70.

Absorbent core 70 may comprise a laminate of fibrous webs and superabsorbent material, or may comprise other suitable structure operative to maintain superabsorbent material fixed in position at desirable locations in the absorbent body.

The high-absorbency material in absorbent core 70 can be selected from natural, synthetic and/or modified natural polymers and/or other materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

In FIG. 2, elastic elements 71 are disposed between and secured to at least one of backsheet 64 and bodyside liner 68 in at least crotch portion 22 of personal care article 12. Elastic elements 71 provide elasticity for absorbent structure 52 in longitudinal direction "L". Such optional elastic elements 71 can provide resilient stretchability or additional resilient stretchability in longitudinal direction "L" for absorbent structure 52. Materials suitable for forming elastic elements 71 include LYCRA® strands, ribbons, or one or more layers or layer elements of a polymeric and/or elastomeric material which may be adhered in personal care article 12, thereby forming resilient stretch in crotch portion 22, while the elastic elements are in a stretched condition.

In some embodiments, opposing left and right spaced containment flaps (not shown) can extend longitudinally along the length of personal care article 12 inwardly of respective side edges of the personal care article. In such embodiments, the containment flaps are typically secured to bodyside liner 24. One example of containment flaps is set forth in U.S. Pat. No. 4,704,116 issued Nov. 3, 1987 to K. Enloe, the disclosure of which is hereby incorporated by reference in its entirety in a manner that is consistent (not contradictory) herewith.

Containment flaps may, for example, be constructed of a fibrous material which is similar to the material comprising backsheet 64. Other suitable conventional materials, such as polymeric films, may also be employed.

Figure 3:
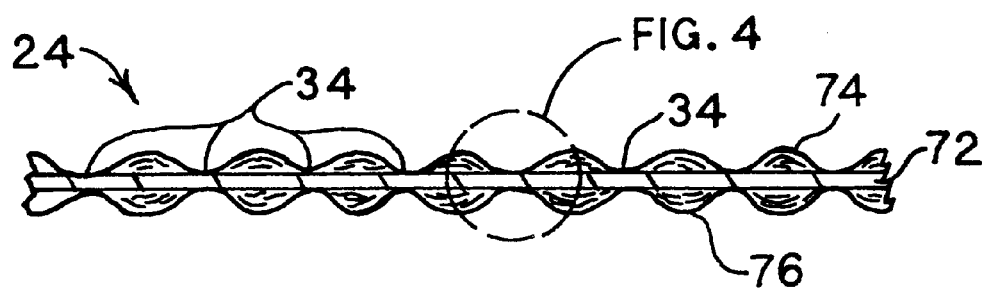
FIG. 3 shows a cross-sectional view of the personal care article of FIG. 1 taken at 3—3 of FIG. 1.
Figure 4:
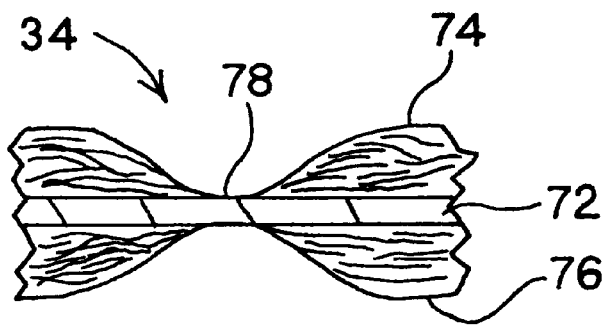
FIG. 4 shows a close-up view of part of the cross-sectional view of FIG. 3.

As shown in FIG. 3, outer cover 24 can comprise a neck bonded laminate (NBL) including an elastomeric film 72 in surface-to-surface relationship with necked spunbonded layers 74, 76 on opposing surfaces of the film. FIG. 3 shows the result of embossing outer cover 24 at spaced locations as shown by embossments 34 penetrating necked spunbonded layers 74, 76. The penetration of embossments 34 densities spunbonded layers 74, 76 against elastomeric film 72 at densified regions 78 (See FIG. 4). Densified regions 78 of spunbonded layers 74, 76 at embossments 34 lock up stretch or extensibility of elastomeric film 72. As respective spunbonded layers 74, 76 are densified by heat and/or pressure during embossing, the spunbonded layers harden and more firmly attach to elastomeric film 72. Thus spunbonded layers 74, 76 lock up elastomeric stretch of film 72 at densified regions 78 of embossments 34. As used herein, "locking up" of stretch means embossments reduce the amount by which the extensible element extends in response to a given extending force because of the embossment created at a surface of the extensible material. Such "locking up" prevents or limits elongation of outer cover 24, or a composite formed by outer cover 24 and another layer, at embossments 34.

Embossments 34 thus increase resistance-to-stretch of outer cover 24 in zones 40, 42, 44, 46 by modifying the physical properties, namely the stretch properties, of the outer cover and thereby locking up at least a portion of the previously available stretch properties. Therefore, in the embodiment of FIG. 1, resistance-to- stretch is greater at zone 40 extending along the length of front portion 14 adjacent front edge 16, and at zone 42 extending along the length of rear portion 18 adjacent rear edge 20, than the resistance-to-stretch at unembossed zones 48, 50.

While unembossed zones 48, 50 are shown as respective defined zones within front portion 14 and rear portion 18 of personal care article 12, the entirety of outer cover 24, except for embossed zones 40, 42, 44, 46 may be considered a second unembossed zone. Namely, in preferred embodiments, outer cover 24 is not embossed at any locations other than at embossments 34. Thus, with the exception of grasping panels 26, 28 and fastener apparatus 30, 32, the resistance-to-stretch is generally uniform over the entirety of outer cover 24. Therefore, in use, embossed zones 40, 42 at the front and rear portions 14, 18 of personal care article 12 provide greater resistance-to-stretch than any unembossed zone or zones inward therefrom, and thereby operate as front and rear waistband sections. Thus, stretch is greater in any other zone or zones and less at front and rear waistband sections, enabling better securement and fit of personal care article 12 to the wearer. Proper operation of waistband sections reduces the likelihood of personal care article 12 leaking exudates, or sliding downward and off the body of the wearer, during movement of the wearer, as a result of too much stretch and freedom of movement of outer cover 24 at the waistband sections of the personal care article.

Embossed zones 40, 42 at the front and rear portions 14, 18 adjacent respective front edge 16 and rear edge 20 provide suitable properties of waist elastics. Thus, such an embodiment is devoid of added waist elastic elements in waistband sections of the front and rear portions 14, 18 of personal care article 12. Outer cover 24 at the first waistband section provides resilient stretch properties typically extant in a waistband elastic element.

Likewise, embossed zones 44, 46 adjacent opposing edges 36, 38 in crotch portion 22 provide greater resistance-to-stretch than the unembossed zone between the embossed zones 44, 46 in crotch portion 22. Therefore, in use, embossed zones 44, 46 resist stretch more than the areas of personal care article 12 between zones 44, 46 and thus provide better seal to the legs of a wearer, to prevent leakage of exudates, than a personal care article having about the same amount of stretch over the entire width of the crotch portion.

Embossed zones 44, 46 in crotch portion 22 can provide the function of leg elastic elements. Therefore, in preferred embodiments, personal care article 12 is devoid of added leg elastic elements in crotch portion 22 of outer cover 24.

In the embodiment of FIG. 1, outer cover 24 is substantially unfolded at front edge 16 and rear edge 20. Any manufacturing process requiring folding of outer cover 24 at the edges would require a complex manufacturing process not preferred for use with this invention.

Resistance-to-stretch of various materials and zones is better described as set forth in the following description of Test Materials, Embossing Process, and Test Procedure.

Test Materials

Materials used as samples in the test procedure are as follows.

1. A resiliently stretchable web comprises a neck bonded laminate (NBL) material having two facing layers of necked spunbonded polypropylene nonwoven webs with necked basis weights of about 20 grams per square meter for each facing. A 35 grams per square meter METALLOCENE# elastomeric resin comprises the core of the three-ply composite laminate (NBL). The METALLOCENE™ elastomeric resin is known as Affinity 58380.00 and available from Dow Chemical Corp. of Midland, Mich. The two facing layers of necked spunbonded polypropylene nonwoven webs are on opposing sides of the elastomeric film core. The composite laminate has a total basis weight of 75 grams per square meter.
2. An extensible material comprises a 24 grams per square meter necked spunbonded polypropylene nonwoven web having about 80% extensibility at 20 grams load per inch width of test sample.
3. A non-extensible material comprises a nonwoven, spunbonded, polypropylene fabric composed of 2.8–3.2 denier fibers formed into a web having a basis weight of 20 grams per square meter.

Test strips made from the above materials have lengths of 25.4 centimeters (10 inches) and widths of 2.54 centimeters (1 inch).

Embossing of Samples

Embossing of test samples utilized embossing equipment comprising a Branson 85 Sonic Bonder with a 0.75 inch wide by 8.0 inch long plunge-type horn and a Branson 1300 P power unit, commercially available from Branson Ultrasonics, a company having offices in Danbury, Conn. Settings for embossing/bonding for all of the test materials are as follows: 70 pounds per square inch (pressure), 85% (full power), 1.0 second (weld time), 2.0 seconds (hold time), and 7.5 down speed. Hold time represents the time the sample is held between anvil 80 and ultrasonic horn (not shown). while the bond or embossment is allowed to cool and solidify.

Figure 5:
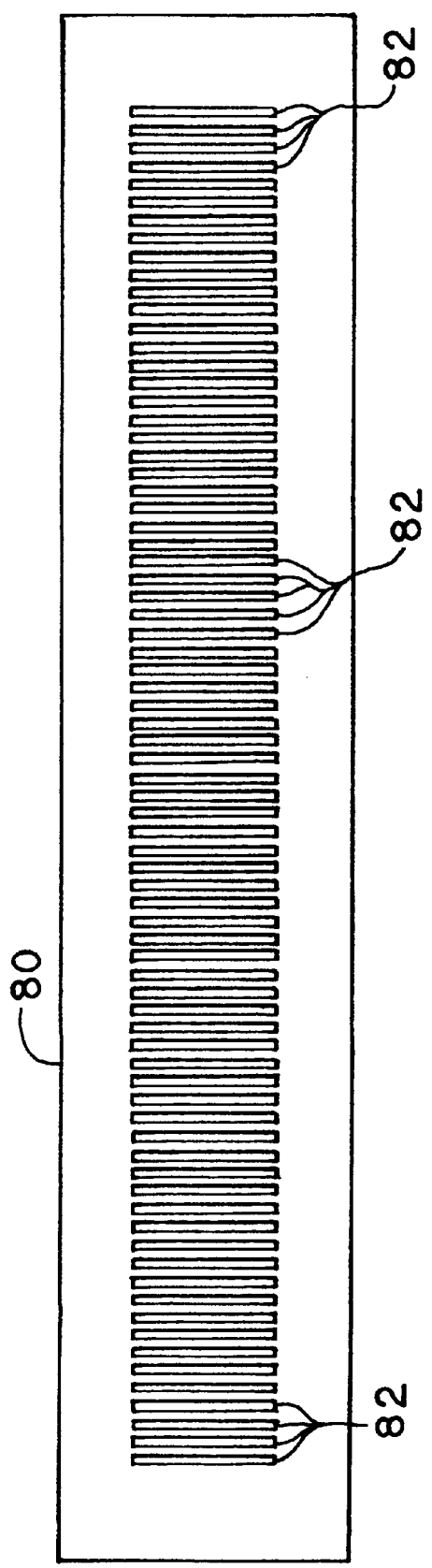
FIG. 5 shows a plan view of the working surface of a plunge-type ultrasonic anvil, including spaced bars.

FIG. 5 shows a plan view of a working surface of a plunge type ultrasonic anvil 80 having a series of working contact bars 82 used with the Branson Sonic Bonder. Bars 82 have lengths of about 19 millimeters (0.75 inch) and width of about 0.8 millimeters (0.031 inch). Thus each bar 82 has a bonding area of about 15.2 square millimeters. Bars 82 are spaced about 1.6 millimeters (0.062 inch) from adjacent bars. When embossing of a 2.54 centimeter (1 inch) wide sample occurs, bars 82 are centered across the width of the sample. Thus about 3.2 millimeters of the sample material on either side of the pattern of embossments is free of embossments.

As shown in FIG. 5, each embossment creating bar 82 extends across the width of the ultrasonic anvil 80. In performing tests, the width of anvil 80 extends along the width of the respective sample. Therefore, embossed samples have embossments shaped as lines or bars extending across the widths of the sample material. Bars 82 comprise 33.6% of the area defined by the 19 millimeter width (0.75 inch) and approximately 178 millimeter (7 inch) length of the array of bars 82. Thus bars 82 densify about 33.6% of the area of the sample contacted within the outline of the array of bars. About 3.2 millimeters of the sample material on either side of the pattern of embossments is not embossed.

Test Procedure

Tensile testing was conducted on a Sintech tensile tester Model #M4011 available from MTS System Corporation of Eden Prairie, Minn.

The test procedure used for determining the tensile load-extension curves, namely the characteristic load/extension properties, of the materials is a modification of ASTM Standard Test Method D882 (Tensile Method for Tensile Properties of Thin Plastic Sheeting). The following modifications are made to the standard ASTM D882 test procedure:

1. The width of all samples is 25.4 millimeters (1.0 inch).
2. The initial separation between jaws of the testing apparatus is 76.2 millimeters (3.0 inches). Therefore, the length of the portion of the sample being tested is 76.2 millimeters.
3. The rate of separation between jaws of the testing apparatus is 50 millimeters/minute for all samples tested.
4. When samples were clamped in jaws of the testing apparatus, the tensile load on the sample being tested, before any tension was applied by movement of the jaws away from each other, was about 10 grams for all samples except for the sample which generated load-extension curve D. The sample which generated load-extension curve D had about 20 grams of load. Such minimal, pre-movement loads were insignificant overall, and are caused, in large part, by tightening the jaws of the testing apparatus.
5. The tensile test for each sample was stopped at an extension of about 60 millimeters for all samples except for the sample which generates load-extension curve D. Namely, the samples were extended to a length of about 180% of their original lengths. However, the sample generating load-extension curve D was stopped at an extension of about 40 millimeters. Thus, the sample generating load-extension curve D was extended to a length of about 152% of its original length.

Tests were conducted as follows. A 2.54 centimeter (1.0 inch) by 25.4 centimeter (10.0 inch) strip or strips of sample material was placed on the tensile tester. Jaws were locked on the ends of the strip of material so that a 7.62 centimeter (3 inch) length of the strip of material was being tested. Stretch along the 7.62 centimeter (3 inch) length was measured as a function of elongation (millimeters) resulting from the amount of force applied (grams).

Test Results

Figure 6:
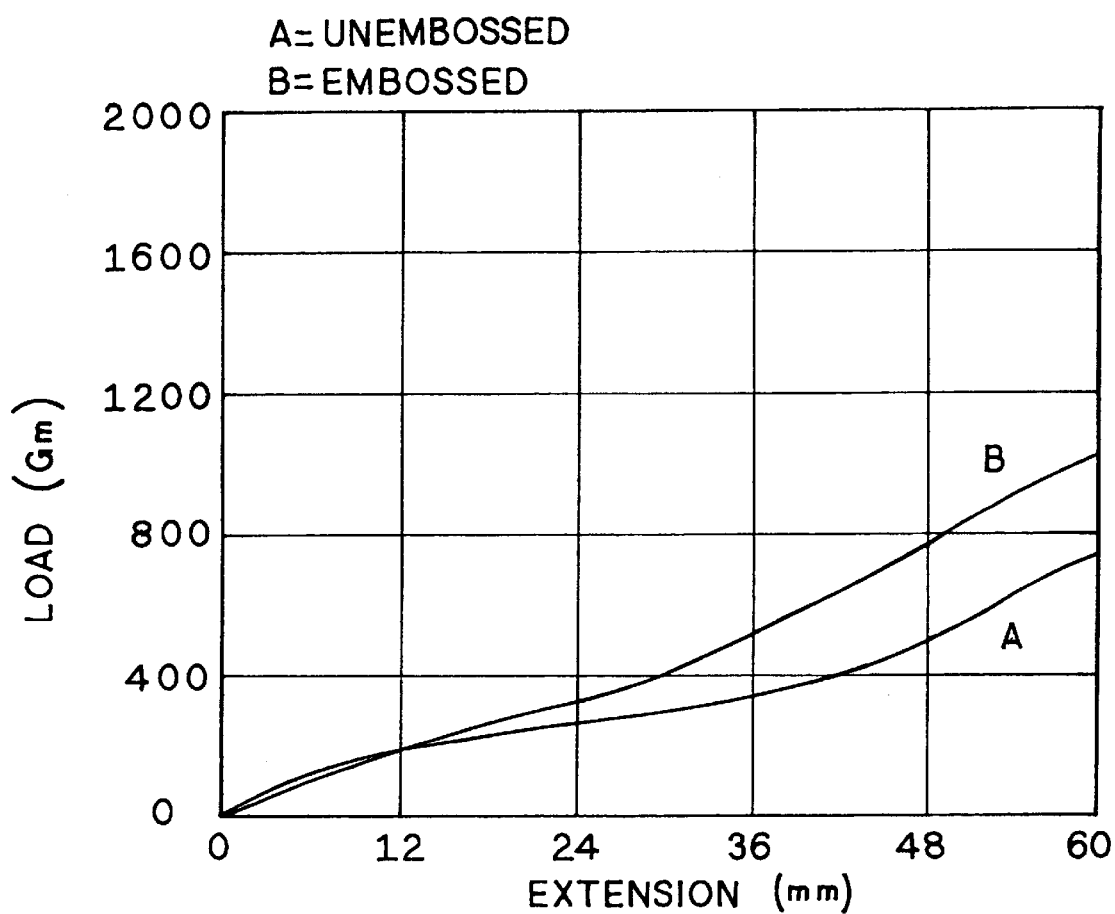
FIG. 6 shows a graph comparing characteristic load/extension relationships of embossed and unembossed areas of the embodiment of FIG. 1.

FIG. 6 shows a graph comparing an unembossed resiliently stretchable panel and a similar but embossed resiliently stretchable panel. The panels comprise neck bonded laminate materials, each including a METALLOCENE™ layer having the characteristics described earlier. Embossing of the embossed panel was done while the panel was in an unstretched condition. No other layers or materials were combined with the embossed panel during embossing or during testing. As shown in FIG. 6, the embossed panel has load-extension curve B showing an increased resistance-to-stretch as compared to load-extension curve A of an unembossed panel made from like material. Thus, the embossing increases the force required to elongate the resiliently stretchable panel. The increased resistance-to-stretch becomes more defined as the elongation distance of the tested panels increases.

Therefore, embossments 34 increase resistance-to-stretch of the embossed zones relative to the unembossed zones.

Figure 7:
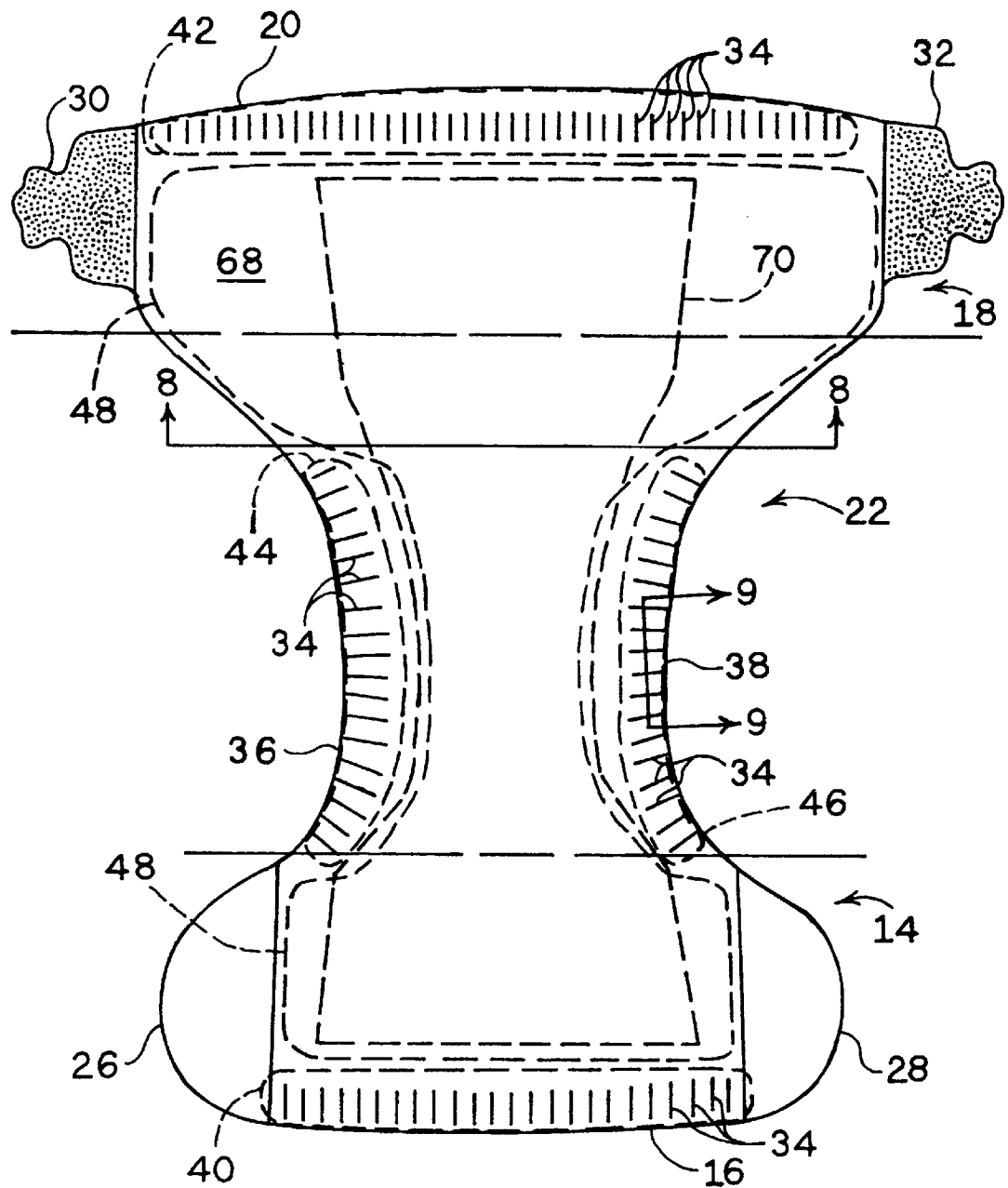
FIG. 7 shows a top view of a second embodiment of personal care articles of the invention having a bodyside liner overlying substantially the entirety of the outer cover.

FIG. 7 shows a second embodiment of the invention. In this embodiment, absorbent structure 52 (of FIG. 1) is replaced with a more conventional absorbent arrangement. Namely, bodyside liner 68 is secured in surface-to-surface relationship with outer cover 24 generally about the outer edges of the outer cover and the bodyside liner, with absorbent core 70 disposed therebetween. The elements illustrated in FIG. 7 have a similar function to the corresponding elements shown in FIG. 1. Further, the elements shown in FIG. 7 can be made of the same materials as described earlier.

Figure 8:
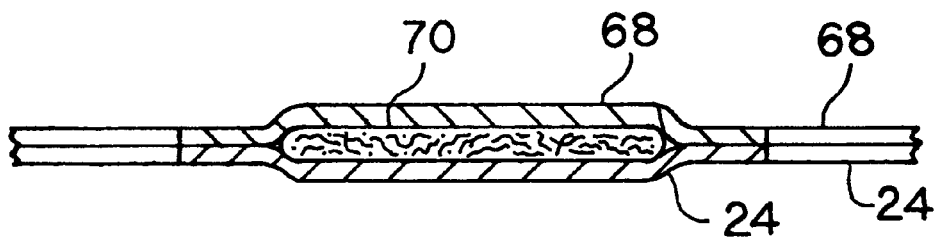
FIG. 8 shows a cross-sectional view of the personal care article of FIG. 7 taken at 8—8 of FIG. 7.

As representatively shown in FIG. 8, bodyside liner 68 and outer cover 24 generally are coextensive and have length and width dimensions which are generally larger than the dimensions of absorbent core 70. As shown in FIG. 7, bodyside liner 68 is associated with and generally superimposed over the entirety of the surface of outer cover 24, the combination of the outer cover and the bodyside liner thereby mutually defining the outer perimeter of personal care article 12. Absorbent core 70 is optionally disposed between outer cover 24 and bodyside liner 68 inboard of the outer perimeter of personal care article 12.

As in the earlier described embodiment, outer cover 24 preferably is resiliently extensible in at least cross-direction "C" at at least front portion 14. However, unlike the earlier embodiment, in FIG. 8, bodyside liner 68 is in surface-to-surface relationship with outer cover 24 and thus is generally extensible in at least cross-direction "C" at least at front portion 14. Such extensibility of bodyside liner 68 is necessary to enable front portion 14, including a portion thereof containing absorbent core 70, to expand or stretch in at least cross direction "C". Such extensibility of bodyside liner 68 can be a function of extensibility of the material used in the bodyside liner, or may be a function of the size, shape, and/or physical structure of the bodyside liner.

Fastener apparatus 30, 32 can be formed as an integral part of outer cover 24 and/or bodyside liner 68. Such incorporation of fastener apparatus 30, 32 reduces the number of elements needed to form personal care article 12.

Figure 9:
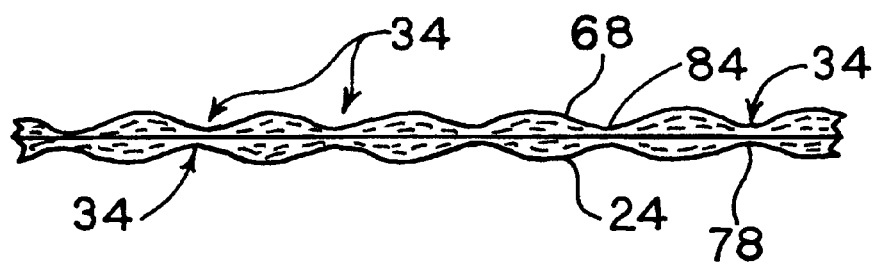
FIG. 9 shows a cross-sectional view of the personal care article of FIG. 7 taken at 9—9 of FIG. 7.

In the embodiment of FIGS. 7–9, bodyside liner 68 can be, for example, a nonwoven, spunbonded polypropylene fabric composed of fibers formed into a web. The fabric can be creped or necked such that the fabric is extensible in at least one of the cross-direction and the longitudinal direction. Bodyside liner 68 can also comprise a stretchable layer, such as a stretch-bonded laminate (SBL) having appropriate elasticity and width to create general overall surface contact between generally the entirety of the body-facing side of personal care article 12 and the body of a wearer. The stretchable layer can be a stretchable film of stretchable material, such as a layer of styrene ethylene butylene styrene copolymer or other elastomeric polymer, or a plurality of strands of a stretchable material such as latex or LYCRA® e.g. secured in stretched condition to a less stretchable layer or web. Other materials having similar properties may also, in the alternative, be provided integral with or attached to bodyside liner 68 to thereby impart the stretch properties. No material, however, should interfere with the soft texture of bodyside liner 68 against the skin of a wearer.

In the embodiment of FIGS. 7–9, outer cover 24 is typically unstretched before being embossed to bodyside liner 68. Thus, as shown in the cross-section of FIG. 9, embossments 34 include densified regions 78, 84. Densified regions 78 at outer cover 24 correspond directly to the densified regions described earlier with respect to the embodiment shown in FIGS. 3 and 4. Densified regions 84, however, comprise regions where bodyside liner 68 is embossed and secured to outer cover 24. At densified regions 84, fibrous materials of bodyside liner 68 are densified by heat, pressure, or the like to both densify the material and to secure the bodyside liner to outer cover 24. Joining of bodyside liner 68 to outer cover 24 is caused, in preferred embodiments, by combined densification and bonding of bodyside liner 68 and the spunbond layer of outer cover 24 in surface-to-surface relationship with the bodyside liner. The spunbonded layer of outer cover 24 and bodyside liner 68, are fused into individual densified layer elements thus bonding outer cover 24 to the bodyside liner at selected embossment loci 34.

While embossments 34 are generally created by heat and/or pressure, adhesives, such as pressure responsive adhesives, can also be utilized to bond outer cover 24 to bodyside liner 68. In such embodiments, there need not be the indentations formed as densified regions 78, 84 and illustrated in FIG. 9. Embossments 34 can comprise adhesives selectively disposed between outer cover 24 and bodyside liner 68. In such embodiments, densified regions 78, 84 need not be present on opposing sides of a substrate formed by outer cover 24 and bodyside liner 68.

As shown in FIG. 7, unembossed zone 48 comprises substantially the entire personal care article 12, except for grasping panels 26, 28, fastener apparatus 30, 32, and embossed zones 40, 42, 44, 46. The embodiment of FIG. 1, although not illustrated, can have an unembossed zone similar to the shape and size of unembossed zone 48 in FIG. 7.

In use, resistance-to-stretch of embossed zone 40 in front portion 14 of personal care article 12 of FIG. 7, is greater than the resistance-to-stretch of zone 48 disposed inwardly from embossed zone 40. The greater resistance-to-stretch results from embossments 34 locking up stretch in outer cover 24 where the outer cover is secured to bodyside liner 68. In zone 40, outer cover 24 preferably is resiliently extensible in cross-direction "C". Thus zone 48 has greater stretchability, and less resistance to stretch, than zone 40, whereby zone 40 acts as a waistband section, fitting and retaining personal care article 12 about the waist of a wearer.

Embossed zone 42 in rear portion 18 functions in substantially the same manner as embossed zone 40 in front portion 14. Outer cover 24 preferably is resiliently extensible at least in cross-direction "C" at least at embossed zones 40, 42. Zones 40 and 42, in combination, act as front and rear waistband sections securing personal care article 12 to the body of the wearer.

Embossed zones 44, 46 in crotch portion 22 extend along and inwardly adjacent respective opposing side edges 36, 38 at leg cut-outs of personal care article 12. At least at crotch portion 22, outer cover 24 and bodyside liner 68 both preferably are resiliently extensible at least in longitudinal direction "L". Embossed zones 44, 46 contain embossments 34, as described earlier, imparting greater resistance-to-stretch in the embossed zones than at the corresponding portion of unembossed zone 48 which is disposed between embossed zones 44, 46. Thus, the unembossed portion of zone 48 disposed between embossed zones 44, 46 has greater stretchability than zones 44, 46 at least in longitudinal direction "L". Embossed zones 44, 46 thus act as leg elastics in providing seal at the legs of the wearer, thus to prevent leakage of exudates from personal care article 12. If zones 44, 46 were unembossed, the amount of sealing effect would be decreased, perhaps nominal, and leakage at crotch portion 22 adjacent the legs of the wearer is more probable.

Test Results

Figure 10:
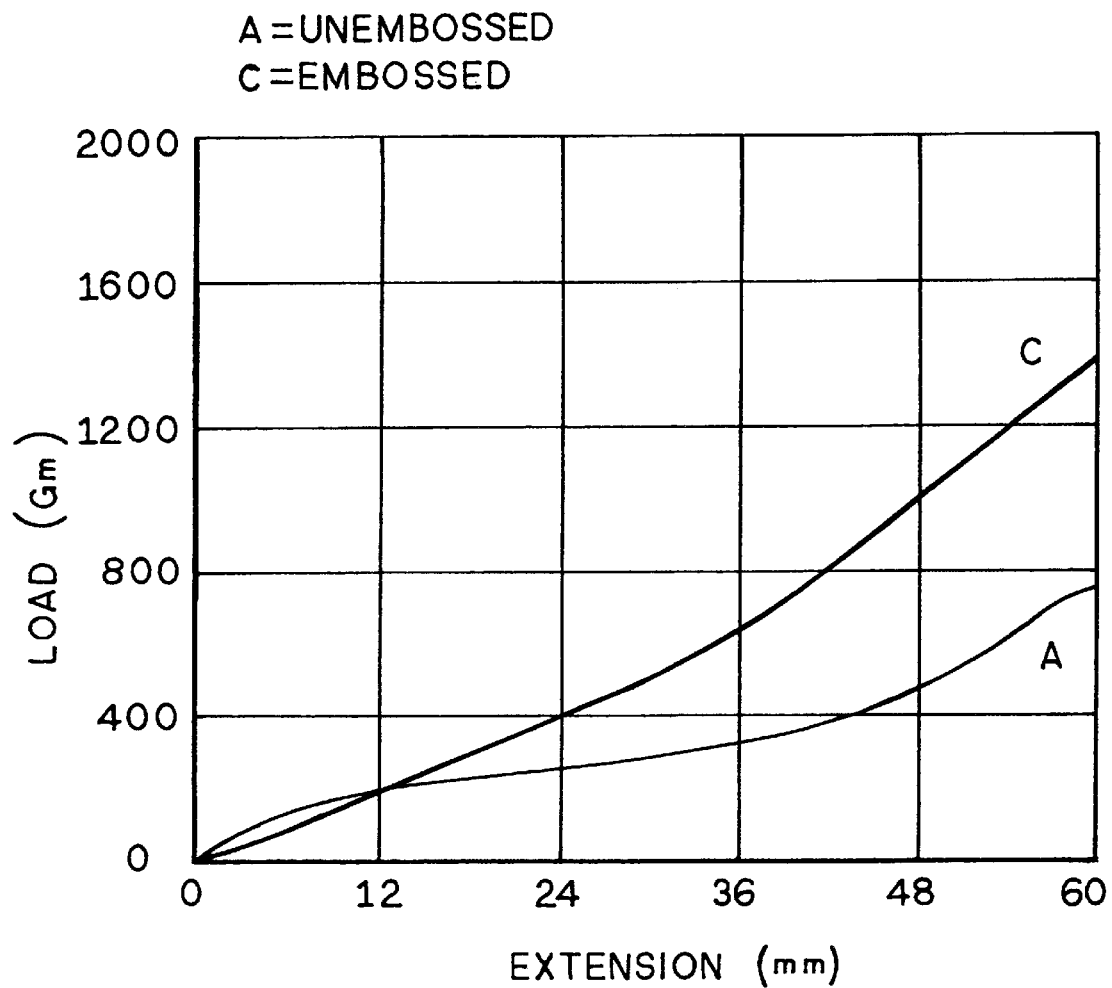
FIG. 10 shows a graph comparing characteristic load/extension relationships of the embossed areas of the embodiment of FIG. 7 to similar but unembossed other panels.

Greater resistance-to-stretch of embossed zones 44, 46 relative to unembossed zone 48 is illustrated in the graph of FIG. 10. The graph of FIG. 10 uses the test materials and procedures described earlier. However, in this embodiment the resiliently stretchable web, described earlier as a neck bonded laminate material having two facing layers of necked spunbonded polypropylene nonwoven webs with necked basis weights of about 20 grams per square meter for each facing, and an elastomeric film core having a basis weight of 35 grams per square meter, was placed on an embossing plate in a non-stretched condition. Then an extensible material, described earlier as a necked spunbonded polypropylene nonwoven web having a basis weight of 4 grams per square meter, is placed over the resiliently stretchable web. A composite, comprising a combination of the resiliently stretchable web and the extensible material, was embossed in the manner described earlier by plunge-type ultrasonic anvil 80 having bars 82 as shown in FIG. 5.

As shown in FIG. 10, embossing of the non-stretched resiliently stretchable panel to the extensible panel increased the resistance to stretch of the composite panel formed by the two joined panels as shown by load-extension curve C when compared to load-extension curve A of an unembossed panel as described earlier.

Figure 11:
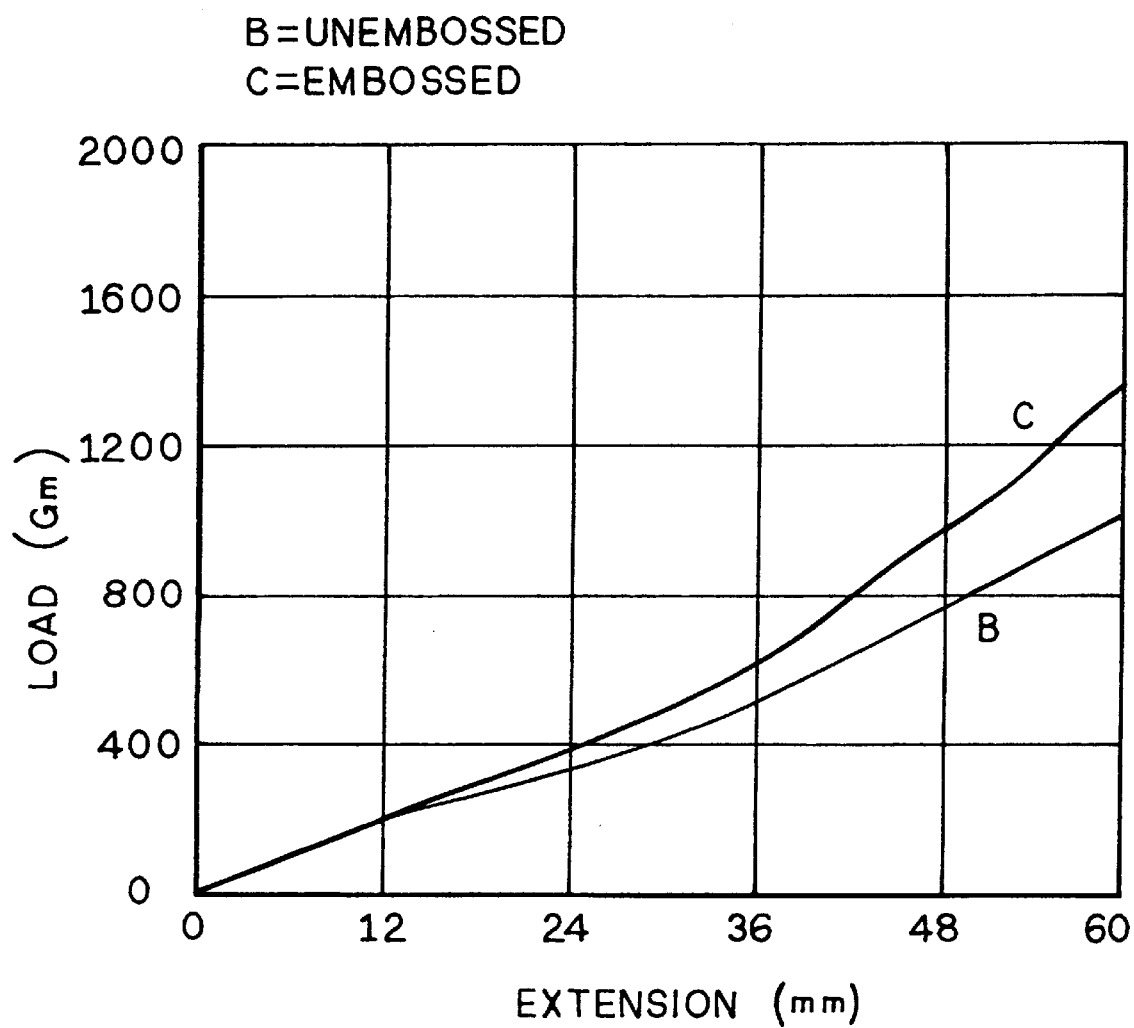
FIG. 11 shows a graph comparing characteristic load/extension relationships of embossed and unembossed areas of the embodiment of FIG. 7.

The resistance-to-stretch for the composite panel is even greater than the resistance-to-stretch for the embossed resiliently stretchable panel identified in FIG. 6 as element B as shown in the graph of FIG. 11. As shown in FIG. 11, load-extension curve C requires more force to elongate the composite material than load-extension curve B as described earlier. The difference in resistance-to-stretch (force to elongate) becomes more significant as the respective panels extend. Therefore, embossing the non-stretched resiliently stretchable panel to the extensible panel creates zones 44, 46 of increased resistance-to-stretch.

Figure 12:
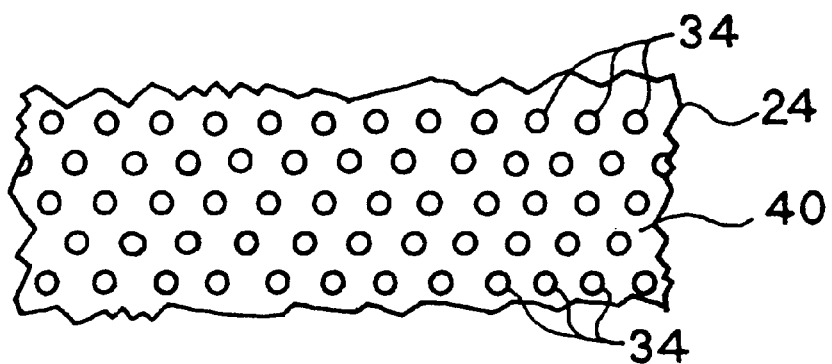
FIG. 12 shows a view of a portion of a surface of a substrate having an array of embossments thereon.

FIG. 12 shows a section of zone 40 for another embodiment of the invention. In this embodiment, embossed zone 40 comprises a plurality of embossments 34 having circular or pin shapes. Embossments 34 comprise an array of multiple rows of embossments. Individual embossments 34 in the array are substantially equally spaced from adjacent embossments. Embossed zone 40 in FIG. 12 functions in a similar manner to embossed zone 40 described in FIG. 7.

While FIGS. 7 and 12 illustrate embossments 34 as series of spaced lines and an array including rows of points, respectively, other patterns or arrays of embossment are contemplated by the invention. For example, the embossments can comprise a pattern of spaced points, crossing lines, straight or curved, continuous or discontinuous, extending in two dimensions across any portion or portions of or across substantially the entirety of the respective embossed zone.

Embossments 34 can comprise between about 5% and about 80% of the total surface area of embossed zones 40 42, 44, 46. In other embodiments, embossments 34 can comprise from about 15% to about 60% of the total surface of the embossed zone. Embossed zones 40, 42, 44, 46 are defined as zones containing embossments having effect on resistance-to-stretch of outer cover 24. Thus, embossed zones 40. 42, 44, 46 can include unembossed areas thereof, and thus include areas of outer cover 24 adjacent embossments 34 or areas located between closely spaced embossments. In the embodiment utilized with the test samples described earlier, about 33.6% of the embossed zone is physically embossed within itself, thus reducing stretchability of a single layer, or is physically embossed to another layer of material.

Embossed zones 40, 42, 44, 46 can be located anywhere on outer cover 24. Further, only one embossed zone 40 need be present on outer cover 24. Likewise, many variations in the patterns shown can be utilized, for example, embossed zones can extend around the perimeter of personal care article 12. Referring especially to the embodiment of FIG. 6, bodyside liner 68 and outer cover 24 must be secured to each other at locations outwardly of absorbent core 70 in order to retain absorbent core 70 in personal care article 12 and to prevent separation of the bodyside liner and outer cover at e.g. edges 16, 20, 36, 38 about the perimeter of the article.

The sizes of embossed zones 40, 42, 44, 46 relative to the overall size of outer cover 24 controls the amount of resistance-to-stretch of the personal care article in the embossed zones and thus the overall resistance-to-stretch of personal care article 12. Embossed zones 40, 42, 44, 46 generally comprise between about 2% and about 50% of the overall area, preferably between about 5% and about 40% of the overall area, and most preferably between about 10% and about 30% of the overall area, of outer cover 24 or a corresponding such panel.

Figure 13:
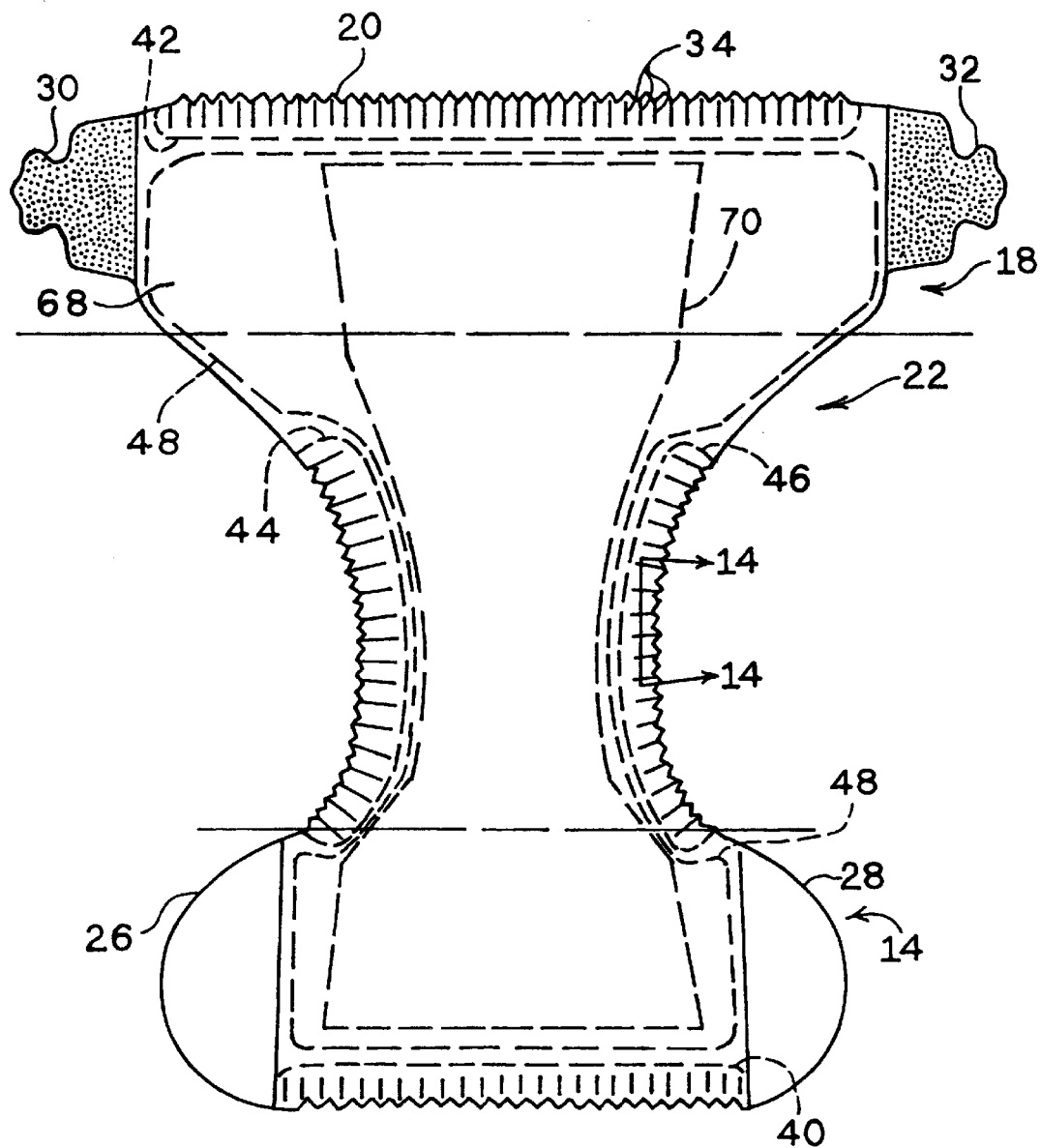
FIG. 13 shows a top view of a third embodiment of personal care articles of the invention similar to the embodiment of FIG. 7 except the outer cover is pre-stretched when secured to the bodyside liner.

FIG. 13 shows a third embodiment of the invention. This embodiment generally corresponds to the embodiment of FIG. 7. However, in this embodiment, outer cover 24 is pre-stretched before being secured to bodyside liner 68.

Figure 14:
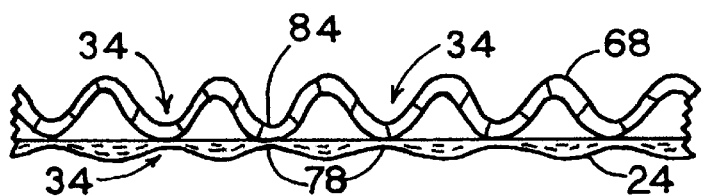
FIG. 14 shows a cross-sectional view of the personal care article of FIG. 13 taken at 14—14 of FIG. 13.

As shown in FIG. 14, pre-stretching of outer cover 24 before securing the outer cover to bodyside liner 68 by the above described embossing causes some wrinkling or pleating of bodyside liner 68. Further, because of the attenuation of resilience resulting from the embossing, after the embossing and after subsequent release of the stretching force, outer cover 24 does not return to its original position.

As in the embodiments described earlier, in this embodiment, embossing increases the resistance-to-stretch of outer cover 24. As described earlier, the substrate comprising outer cover 24 and bodyside liner 68 has a greater resistance-to-stretch at embossed zones 40, 42, 44, 46 than at unembossed zone 48. Accordingly, the embodiment of FIG. 13 functions in a similar manner to the embodiment of FIG. 7.

However, in use, the embodiment of FIGS. 13 and 14 has a two stage load effect. The two stage load effect occurs when, during normal use, the substrate is extended beyond the original pre-stretched length of outer cover 24 which existed when outer cover 24 was secured to bodyside liner 68. At stretch lengths beyond the original pre-stretched length, the amount of force required to continue to extend personal care article 12 is much greater than the amount of force required to stretch the personal care article to the pre-stretch length. Thus, the resistance-to-stretch of the load-extension curve beyond the original length of pre-stretched outer cover 24 is much greater than the resistance-to-stretch of the load-extension curve before the pre-stretched length has been reached. Namely the load/extension ratio increases. Therefore, at extensions beyond the original pre-stretched length of outer cover 24, the resistance-to-stretch increases significantly. While choosing to not be bound by theory, applicants' contemplate that the increased resistance is generated primarily in the embossed zones.

Figure 15:
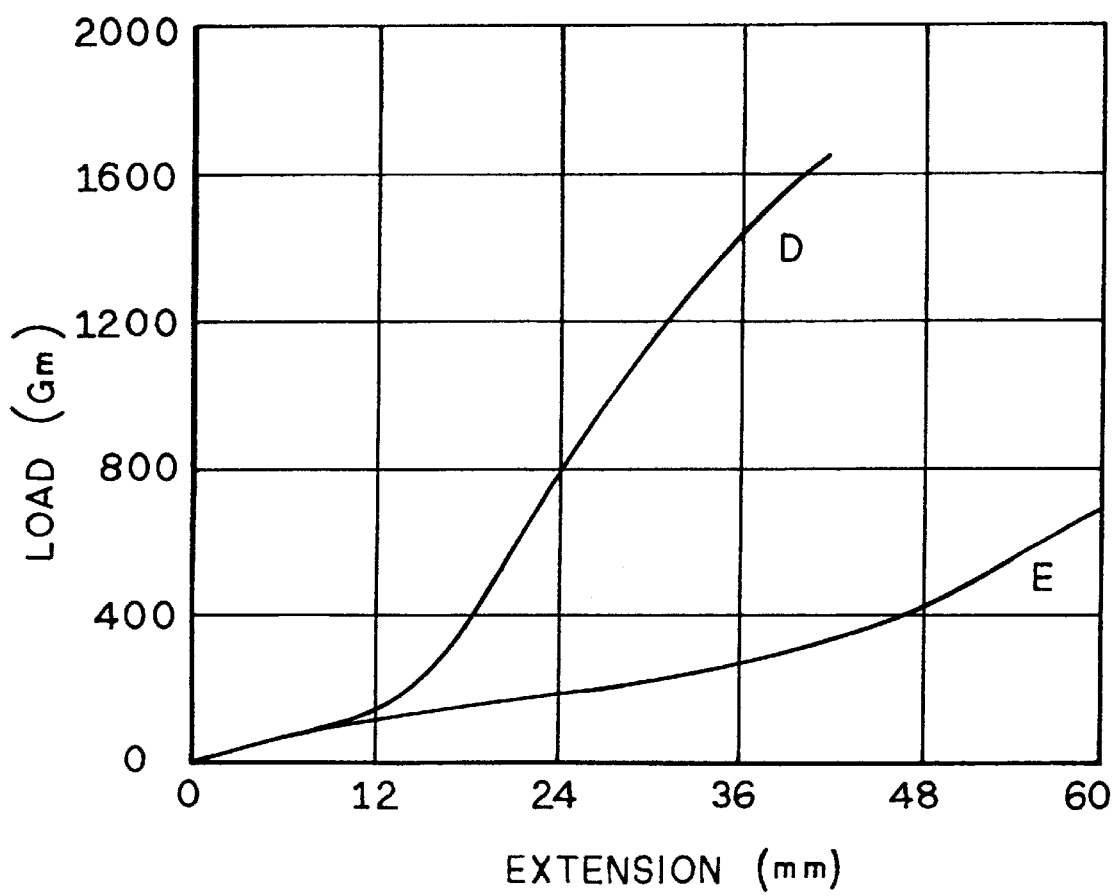
FIG. 15 shows a graph comparing characteristic load/extension relationships of embossed and unembossed areas of the embodiment of FIG. 13.

Such a two stage effect is clearly illustrated in the graph of FIG. 15 which shows operation of a substrate comprising the resiliently stretchable layer described earlier and test strip wherein the outer cover layer was pre-stretched by 50% of its original length before being embossed to a non-extensible panel as described earlier. Embossing of the resiliently stretchable panel to the non-extensible panel created a composite panel. Since a length of 7.62 centimeters (3 inches) of the composite panel was tested by the tensile tester, the overall length of that section of the resiliently stretchable panel, when pre-stretched and secured to the non-extensible panel comprised about 11.4 centimeters. Therefore, as expected, FIG. 15 shows a change in the resistance-to-stretch of load-extension curve D at an elongation of about 11 to about 12 centimeters. At this region of the load-extension curve, the slope of load-extension curve D increases greatly finishing at a value of about 1600 grams of force for an elongation of about 40 millimeters.

Thus two-stage curve D is created by pre-stretching and securing the resiliently extensible panel to the non-extensible panel. The region of the load-extension curve where the slope changes can be controlled by the amount of pre-stretching of the resiliently extensible panel when secured to the non-extensible panel.

In FIG. 15, the result of the composite panel is also compared to an otherwise resiliently stretchable panel that is pre-stretched to about 50% of its original length and then removed without securement. As expected, the load-extension curve E of the panel that is merely pre-stretched, has much less resistance-to-stretch than the composite panel that has been pre-stretched and secured/embossed. The greater resistance-to-stretch for curve D is because the pre-stretched layer is secured to a non-extensible panel. At lengths beyond the original pre-stretched length, the non-extensible panel will greatly resist further extension of the composite panel. Thus, comparison to a resiliently stretchable panel shows greater resistance-to-stretch in the composite panel.

Embossing selected zones of a resiliently stretchable panel to a non-extensible panel when the resiliently stretchable panel is pre-stretched provides the embossed zones with greater resistance-to-stretch than unembossed zones and provides a two stage tensile load-extension curve, where the second stage exhibits a greater incremental resistance to stretch than the first stage, and begins at substantially the pre-stretched length of the resiliently stretchable panel.

The distance the resiliently stretchable panel is pre-stretched can be used to control the point (elongation distance) where the two stage curve has a much greater resistance-to-stretch. In embodiments where the second panel is pre-stretched, the second panel generally is elongated no more than about 350% and not less than about 5% of its original length, preferably no more than about 200% and not less than about 10% of its original length, and most preferably no more than about 100% and not less than about 15% of its original length, when secured to the first panel.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, such is not meant to include there, or in the instant specification, anything not structurally equivalent to what is shown in the embodiments or otherwise disclosed in the specification.

Having thus described the invention, what is claimed is:

1. A personal care article having a lateral cross-direction and a lengthwise longitudinal direction, a front portion, a rear portion, and a crotch portion interconnecting the front and rear portions, said personal care article comprising:
   (a) an outer cover resiliently stretchable in at least one direction, at least a first portion of a first zone of said resiliently stretchable outer cover having a pattern of embossments, effective to reduce stretchability of said outer cover in the first zone, thereby to provide a first set of desired properties pertaining to stretch of said outer cover, said resiliently stretchable outer cover having at least a second zone wherein said outer cover is not modified to provide the first set of properties, said embossments in the first zone thus causing the first zone to have a different resistance-to-stretch than the second zone.

2. A personal care article as in claim 1, said outer cover having resilient stretchability in at least the cross-direction in the front portion of said personal care article, said outer cover having a first waistband section in the front portion and a second waistband section in the rear portion, the first zone comprising the first waistband section in the front portion of said personal care article, the first waistband section having a greater resistance-to-stretch than the second zone, the first waistband section providing the first set of desired stretch properties pertaining to the amount of stretch in the waistband section.

3. A personal care article as in claim 2, the second zone comprising an area of said outer cover spaced inwardly from the first waistband section toward the crotch portion, the second zone being generally free from embossments.

4. A personal care article as in claim 2, the first waistband section being devoid of added waist elastic elements.

5. A personal care article as in claim 2, said outer cover being resiliently stretchable in at least the cross-direction in the rear portion of said personal care article, the second waistband section comprising a third zone in the rear portion of said personal care article, the second waistband section having a greater resistance-to-stretch than the second zone.

6. A personal care article as in claim 5, said outer cover including a fourth zone and a fifth zone, the fourth and fifth zones being effectively embossed at portions thereof such that the fourth and fifth zones have greater resistance-to-stretch than the second zone.

7. A personal care article as in claim 6, said personal care article having first and second outer edges at opposing sides of the crotch portion, the fourth zone being adjacent the first outer edge at least in the crotch portion and the fifth zone being adjacent the second outer edge at least in the crotch portion of said personal care article.

8. A personal care article as in claim 7, the fourth and fifth zones extending along the length of the crotch portion in the longitudinal direction.

9. A personal care article as in claim 8, said personal care article being devoid of added leg elastic elements in the crotch portion.

10. A personal care article as in claim 7, the fourth and fifth zones providing the properties of leg elastic elements.

11. A personal care article as in claim 1, the first zone of said outer cover comprising a plurality of spaced embossments forming an array of such embossments.

12. A personal care article as in claim 11, the array comprising at least two rows of spaced points.

13. A personal care article as in claim 11, the array comprising a series of spaced lines.

14. A personal care article as in claim 1, said outer cover being resiliently stretchable in at least the longitudinal direction in the crotch portion, said personal care article having first and second outer edges at opposing sides of the crotch portion, the first zone being adjacent said first outer edge at least in the crotch portion of said personal care article.

15. A personal care article as in claim 14, said outer cover being embossed at a third zone adjacent said second outer edge at least in the crotch portion of said personal care article, the third zone having a greater resistance-to-stretch than the second zone.

16. A personal care article as in claim 15, the first zone and the third zone each extending along the length of the crotch portion in the longitudinal direction.

17. A personal care article as in claim 16, the second zone being located between the first zone and the third zone at least in the crotch portion of said personal care article.

18. A personal care article as in claim 1, said personal care article having a front edge at the front portion, and a rear edge at the rear portion, said outer cover being substantially unfolded at said front edge and said rear edge.

19. A personal care article as in claim 1, said personal care article including an absorbent structure superposed on and operably connected to said outer cover to form an absorbent said personal care article.

20. A personal care article as in claim 19, said absorbent structure including a substantially liquid impermeable backsheet, a liquid permeable bodyside liner superposed on said backsheet, and an absorbent core disposed between said bodyside liner and said backsheet.

21. A personal care article as recited in claim 20, said personal care article further comprising extendible attachment elements securing said absorbent structure to said outer cover while allowing resilient stretching of said outer cover along the cross-direction.

22. A personal care article as in claim 21 wherein said extendible attachment elements each have at least one pleat folded therein that connects said absorbent structure to said outer cover.

23. A personal care article as in claim 1, said outer cover being intermittently embossed in the first zone.

24. A personal care article having a lateral cross-direction and a lengthwise longitudinal direction, a front portion, a rear portion, and a crotch portion interconnecting the front and rear portions, said personal care article comprising:
   (a) a first panel;
   (b) a second panel resiliently stretchable in at least one direction, said resiliently stretchable second panel being in surface-to-surface relationship with said first panel, said first panel and said second panel, in combination, defining a substrate, at least a first portion of a first zone of said second panel having a pattern of embossments securing said second panel to said first panel and thereby reducing stretchability of said second panels, a second zone wherein said second panel does not exhibit embossments securing said second panel to said first panel or the first set of properties, said embossments in the first zone thus causing the first zone to have a different set of stretch properties than the second zone.

25. A personal care article as in claim 24, said second panel being unstretched when secured to said first panel.

26. A personal care article as in claim 24, the first zone comprising at least part of the crotch portion of said personal care article, the first zone at the crotch portion having a greater resistance-to-stretch than the second zone.

27. A personal care article as in claim 26, wherein said personal care article is devoid of added leg elastic elements in the crotch portion.

28. A personal care article as in claim 26, at least a first portion of a third zone of said second panel having a pattern of embossments securing said second panel to said first panel.

29. A personal care article as in claim 28, the crotch portion having first and second opposing edges at first and second opposing leg cut-outs in the crotch portion, the first zone and the third zone being located adjacent said first and second opposing edges in at least the crotch portion.

30. A personal care article as in claim 29, the second zone being disposed between the first and third zones, the first and third zones having greater resistance-to-stretch than the second zone.

31. A personal care article as in claim 24, the first zone of said second panel comprising a plurality of spaced patterns of embossments forming an array of embossments.

32. A personal care article as in claim 31, the array comprising at least two rows of spaced points.

33. A personal care article as in claim 31, the array comprising a plurality of spaced embossed lines.

34. A personal care article as in claim 24, said first panel comprising an extensible bodyside liner.

35. A personal care article as in claim 34, said second panel comprising an outer cover.

36. A personal care article as in claim 24, said first panel comprising a substantially non-extensible bodyside liner.

37. A personal care article as in claim 36, said resiliently stretchable second panel comprising an outer cover.

38. A personal care article as in claim 37, said outer cover being pre-stretched in at least one direction when secured to said bodyside liner.

39. A personal care article as in claim 24, said outer cover being resiliently stretchable in at least the cross-direction in the front portion of said personal care article, said outer cover having a first waistband section in the front portion and a second waistband section in the rear portion, the first zone comprising said first waistband section in the front portion of said personal care article, said first waistband section having a greater resistance-to-stretch than the second zone, said first waistband section providing the first set of desired properties pertaining to the amount of stretch in said waistband section.

40. A personal care article as in claim 39, the second zone comprising an area of said outer cover spaced inwardly from said first waistband section toward the crotch portion.

41. A personal care article as in claim 39, said first waistband section being devoid of added waist elastic elements.

42. A personal care article as in claim 39, said outer cover being resiliently stretchable in at least the cross-direction in the rear portion of said personal care article, said second waistband section comprising a third zone in the rear portion of said personal care article, the third zone in said second waistband section having a greater resistance-to-stretch than the second zone.

43. A personal care article as in claim 38, said outer cover being pre-stretched to a predetermined degree of elongation before securement to said bodyside liner, said substrate having a first characteristic load/extension relationship when stretched to the predetermined degree of elongation, and a second different load/extension relationship when stretched beyond the predetermined degree of elongation.

44. A personal care article as in claim 24 wherein the pattern of embossments in the first zone controls the resistance-to-stretch of said personal care article in the first zone.

45. A personal care article as in claim 24 wherein the first zone comprises between about 2% and about 50% of the overall area of said second panel.

46. A personal care article as in claim 24 wherein the first zone comprises between about 5% and about 40% of the overall area of said second panel.

47. A personal care article as in claim 24 wherein the first zone comprises between about 10% and about 30% of the overall area of said second panel.

48. A personal care article as in claim 24 wherein about 5% to about 80% of the surface area in the first zone of said second panel is embossed to said first panel.

49. A personal care article as in claim 48 wherein said embossments provide bonding of said second panel to said first panel as a pattern of spaced points extending in two dimensions across substantially the entirety of the first zone.

50. A personal care article as in claim 49 wherein the bonding comprises ultrasonic bonding of said second panel to said first panel.

51. A personal care article as in claim 48 wherein said embossments comprise adhesive bonding of said second panel to said first panel.

52. A personal care article as in claim 24 wherein said second panel is elongated no more than about 350% and not less than about 5% when secured to said first panel.

53. A personal care article as in claim 24, wherein said second panel is elongated no more than about 200% and not less than about 10% when secured to said first panel.

54. A personal care article as in claim 24, wherein said second panel is elongated no more than about 100% and not less than about 15% when secured to said first panel.

55. A method of imparting first and second different sets of stretch properties to respective first and second different zones of a substrate of a personal care article, the substrate including a first panel and a second resiliently stretchable panel, the method comprising securing the first panel in surface-to-surface relationship with the second panel by effectively embossing at least portions of a first zone of the second panel to respective portions of the first panel, the embossing causing the first zone of securement to have reduced stretchability compared to a second substantially unembossed zone of the substrate.

56. A method as in claim 55 wherein the second panel is unstretched when secured to the first panel.

57. A method as in claim 55 wherein the first zone has a greater resistance-to-stretch than the second zone.

58. A method as in claim 55, including embossing the second panel to the first panel at a third zone, the third zone having a different resistance-to-stretch than the second zone.

59. A method as in claim 58 wherein the third zone has a greater resistance-to-stretch than the second zone.

60. A method as in claim 58 where the second zone is disposed between the first and third zones.

61. A method as in claim 55 wherein the first zone comprises a plurality of spaced embossment patterns forming an array comprising at least two rows of spaced points.

62. A method as in claim 61 wherein the first zone array comprises a plurality of spaced embossed lines.

63. A method as in claim 55 wherein the first panel comprises an extensible bodyside liner.

64. A method as in claim 63 wherein the second panel comprises a resiliently stretchable outer cover.

65. A method as in claim 64 wherein the first panel comprises a substantially non-extensible bodyside liner.

66. A method as in claim 65 wherein the second panel comprises an outer cover.

67. A method as in claim 55, including pre-stretching the second panel and securing the second panel to the first panel in the pre-stretched condition.

68. A method as in claim 67 including pre-stretching the second panel no more than about 350% and not less than about 5% before securement to the first panel at portions of the first zone.

69. A personal care article having a lateral cross-direction and a lengthwise longitudinal direction, a front portion, a rear portion, and a crotch portion interconnecting the front and rear portions, said personal care article comprising:

(a) a first panel;

(b) a second panel resiliently stretchable in at least one direction, said resiliently stretchable second panel being pre-stretched to a predetermined degree and being secured in surface-to-surface relationship with said first panel in the pre-stretched condition, said first panel and said second panel, in combination, defining a substrate, said substrate exhibiting a first characteristic load/extension relationship, representing a first incremental resistance to stretch, when being stretched to the predetermined degree of elongation, and a second greater characteristic load/extension relationship, representing a second greater incremental resistance to stretch, when stretched beyond the predetermined degree of elongation, wherein securement between said second panel and said first panel comprises a pattern of embossments providing a first set of desired properties pertaining to stretch of a first zone of said second panel, said personal care article including a second zone wherein the second panel does not exhibit embossments securing said second panel to said first panel, or the first set of properties, said embossments in the first zone thus causing the first zone to have a different resistance-to-stretch than the second zone.

70. A personal care article as in claim 69 wherein said first panel comprises a bodyside liner and said second panel comprises an outer cover.

71. A personal care article as in claim 70, said outer cover being resiliently stretchable in at least the cross-direction in the front portion of said personal care article, said outer cover having a first waistband section in the front portion and a second waistband section in the rear portion, the first zone comprising the first waistband section in the front portion of said personal care article, the first waistband section having a greater resistance-to-stretch than the second zone, the first waistband section providing the first set of desired stretch properties pertaining to the amount of stretch in the waistband section.

72. A personal care article as in claim 71, the second zone comprising an area of said outer cover spaced inwardly from the first waistband section toward the crotch portion.

73. A personal care article as in claim 71, the first waistband section being devoid of added waist elastic elements.

74. A personal care article as in claim 71, said outer cover being resiliently stretchable in at least the cross-direction in the rear portion of said personal care article, the second waistband section comprising a third zone in the rear portion of said personal care article, the third zone in the second waistband section having a greater resistance-to-stretch than the second zone.

* * * * *